United States Patent [19]

Najer

[11] 4,261,998
[45] Apr. 14, 1981

[54] TETRAHYDRO-ISOQUINOLINE DERIVATIVES

[75] Inventor: Henry Najer, Paris, France
[73] Assignee: Synthelabo, Paris, France
[21] Appl. No.: 93,202
[22] Filed: Nov. 13, 1979

Related U.S. Application Data

[62] Division of Ser. No. 39,446, May 15, 1979, abandoned.

[30] Foreign Application Priority Data

May 18, 1978 [FR] France ................. 78 14804

[51] Int. Cl.³ .................. A61K 31/47; C07D 217/00
[52] U.S. Cl. ........................ 424/258; 546/146; 546/149
[58] Field of Search ........................... 424/258

[56] References Cited

U.S. PATENT DOCUMENTS

| 3,337,539 | 8/1967 | Meszaros et al. ............... 546/149 |
| 3,562,280 | 2/1971 | Leimgruber et al. ............ 546/149 |

FOREIGN PATENT DOCUMENTS 2054483  4/1971  France .
2059979 11/1971  France ................................ 424/258
2215948  8/1974  France .

*Primary Examiner*—Jose Tovar
*Assistant Examiner*—James H. Turnipseed
*Attorney, Agent, or Firm*—Stevens, Davis, Miller & Mosher

[57] ABSTRACT

2-(2-Chlorobenzyl)-1,2,3,4-tetrahydroisoquinoline of the formula

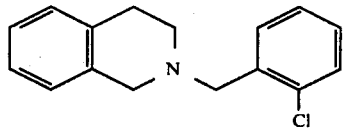

and its pharmaceutically acceptable addition salts, are useful for the treatment of arterial or venous thrombosis. They can be prepared by reducing the amide 2-(2-chlorobenzoyl)-1,2,3,4-tetrahydroisoquinoline, for example with boron hydride in an inert organic solvent, and optionally converting a free amine thereby produced into a salt.

2 Claims, No Drawings

TETRAHYDRO-ISOQUINOLINE DERIVATIVES

This is a division of application Ser. No. 39,446 filed May 15, 1979, now abandoned.

The present invention relates to a tetrahydroisoquinoline derivative, its pharmaceutically acceptable acid addition salts, its preparation and its use in therapy.

The tetrahydroisoquinoline derivative of the invention is 2-(2-chlorobenzyl)-1,2,3,4-tetrahydroisoquinoline of the formula

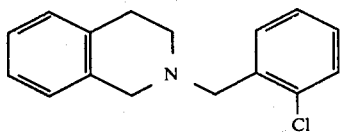

(1)

The pharmaceutically acceptable addition salts of this compound also form part of the invention.

The invention also provides a process for the preparation of the compounds of the invention, which comprises reducing the amide of formula

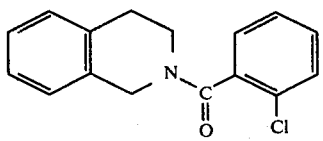

(2)

The reduction can be carried out with boron hydride in an inert organic solvent, for example. Preferably the reaction mixture is heated.

The free amine can, of course, be converted into an acid addition salt. Methods for such conversion are per se well known. The process of preparing the compounds of the invention will frequently be carried out to yield the free amine, in which event it includes the optional further step of converting it into an acid addition salt.

The compounds of the invention can be used for the treatment of all forms of arterial or venous thrombosis.

Pharmaceutical compositions containing a compound of the invention, together with a pharmaceutically acceptable excipient, especially for oral or parenteral administration, form part of the invention.

The daily posology will usually range from 200 to 1,000 mg/day.

The following Example illustrates the invention.

EXAMPLE 1. 2-(2-Chlorobenzoyl)-1,2,3,4-tetrahydroisoquinoline 26.08 g of 2-chlorobenzoyl chloride were reacted with 44.33 g (0.6 mol) of 1,2,3,4-tetrahydroisoquinoline in chloroform overnight, whilst stirring. After the chloroform had been driven off, the resulting solid was recrystallised from isopropyl alcohol.

2. 2-(2-Chlorobenzyl)-1,2,3,4-tetrahydroisoquinoline and its hydrochloride

A solution, in tetrahydrofuran, of the amide obtained above, of formula (2) was added dropwise, under nitrogen and whilst stirring, to a solution, placed in an ice-bath, of 65 ml of boron hydride ($BH_3$) in tetrahydrofuran. When the addition was complete, the mixture was heated to the reflux temperature in the course of one hour and left under reflux overnight. Water and then a 10% strength aqueous solution of HCl were added in order to destroy the complexes formed. The solution was heated under reflux for a further 90 minutes and the THF was then evaporated off. The resulting aqueous solution was extracted twice with ethyl acetate, made alkaline with sodium hydroxide and then extracted with diethyl ether. The ether layer was washed with water until the pH of the washings was 7, and the ether was then evaporated. The resultant oil was taken up in ethyl alcohol. Hydrogen chloride was bubbled through the mixture at 0° C., whilst stirring. The solution was evaporated to give a solid which was washed with ether. This solid, 2-(2-chlorobenzyl)-1,2,3,4-tetrahydroisoquinoline hydrochloride, melts at 190°–2° C.

This compound was studied pharmacologically and found to exhibit an inhibitory action on platelet aggregation. Its acute toxicity, determined on mice by oral administration, is 280 mg/kg.

I claim:

1. A method of inhibiting platelet aggregation in a patient, which comprises administering to said patient an effective amount of 2(2-chlorobenzyl)-1,2,3,4-tetrahydro-isoquinoline or a pharmaceutically acceptable salt thereof.

2. A method of claim 1, wherein said effective amount is from 200 to 1,000 mg per day.